United States Patent
Skalli et al.

(10) Patent No.: US 7,241,045 B2
(45) Date of Patent: Jul. 10, 2007

(54) STEREORADIOGRAPHY DEVICE AND METHOD FOR THE USE THEREOF

(75) Inventors: Wafa Skalli, Paris (FR); Raphaël Dumas, Paris (FR); David Mitton, Kremlin Bictre (FR); Philippe Bataille, Paris (FR); Damien Quidet, Meaux (FR)

(73) Assignees: Centre National de la Recherche Scientifique, Paris (FR); Ecole Nationale Superieure d'Arts et Metiers, Paris (FR)

( * ) Notice: Subject to any disclaimer, the term of this patent is extended or adjusted under 35 U.S.C. 154(b) by 72 days.

(21) Appl. No.: 10/515,230

(22) PCT Filed: May 23, 2003

(86) PCT No.: PCT/FR03/01576

§ 371 (c)(1),
(2), (4) Date: Mar. 3, 2005

(87) PCT Pub. No.: WO03/099124

PCT Pub. Date: Dec. 4, 2003

(65) Prior Publication Data

US 2005/0147206 A1     Jul. 7, 2005

Related U.S. Application Data

(60) Provisional application No. 60/382,372, filed on May 23, 2002.

(51) Int. Cl.
*G01D 18/00* (2006.01)
*H05G 1/61* (2006.01)

(52) U.S. Cl. .................. 378/207; 378/41; 378/164; 378/208

(58) Field of Classification Search .................. 378/41, 378/164, 207, 208
See application file for complete search history.

(56) References Cited

U.S. PATENT DOCUMENTS 4,719,646 A    1/1988  Saunders et al.

(Continued)

FOREIGN PATENT DOCUMENTS

FR    2 720 930 A    12/1995

(Continued)

*Primary Examiner*—Edward J. Glick
*Assistant Examiner*—Thomas R. Artman
(74) *Attorney, Agent, or Firm*—Connolly Bove Lodge & Hutz LLP

(57) ABSTRACT

A calibration system is disclosed for a stereoradiographic device having an X-ray source and a vertical X-ray receiver, the calibration system includes a horizontal table which rotates between two reference positions that are separated by 90 degrees in a horizontal plane of the table. A vertical frame is fastened to the horizontal table and is symmetrical with an axis of rotation of the table, the frame accommodates a patient that remains stationary relative to the frame as the table is rotated between its two reference positions wherein corresponding X-ray photographs are taken. At least three markers made of radio-opaque material are firmly attached to the frame, one of the markers represents the origin of orthogonal X,Y and Z axes, a second of the markers is located at a predetermined point along the X-Y axes, the third marker located at a known distance along the Z axis, the markers defining respective distances Lx, Ly or H relative to the origin.

11 Claims, 3 Drawing Sheets

U.S. PATENT DOCUMENTS

| | | | |
|---|---|---|---|
| 5,967,982 A * | 10/1999 | Barnett | 600/429 |
| 6,044,132 A | 3/2000 | Navab | |
| 6,050,724 A * | 4/2000 | Schmitz et al. | 378/205 |
| 6,055,449 A | 4/2000 | Navab | |
| 6,079,876 A * | 6/2000 | Schuetz | 378/205 |
| 6,381,302 B1 * | 4/2002 | Berestov | 378/41 |
| 6,510,198 B2 * | 1/2003 | Simon et al. | 378/62 |
| 2001/0039421 A1 | 11/2001 | Heilbrun et al. | |

FOREIGN PATENT DOCUMENTS

WO     WO 01 50956 A1     7/2001

\* cited by examiner

STEREORADIOGRAPHY DEVICE AND METHOD FOR THE USE THEREOF

FIELD OF THE INVENTION

The present invention relates to a stereoradiography device allowing the calibration of radiographs which constitutes the essential prerequisite in the reconstruction of a three-dimensional image on the basis of two photographs obtained in two dimensions and, in particular, to a stereoradiography device designed for positioning the subject to be radiographed and to be interposed between an X-ray source and a receiver of the said rays, comprising a horizontal table that is mobile in rotation and/or in translation in a single direction. The present invention also relates to the method of calibrating and of using the said device.

BACKGROUND OF THE INVENTION

There are many publications and patents which disclose the possibility for reconstructing an object in three dimensions on the basis of photographs obtained in two dimensions. This is in particular the case of stereovision. Stereoradiography, or multi-planar radiography, is based on the same principles, the third dimension is given by the mapping of at least two views taken at different angles of incidence and this mapping is not possible without a calibration stage which, in stereovision, is most often carried out once and for all before the images are taken. In the field of radiography, these different angles of incidence impose either the use of several X-ray sources or a spatial displacement of a single source or a displacement of the subject to be radiographed in front of this single source.

Now, in the field of clinical radiography, the simultaneous use of two X-ray sources is extremely rare. Furthermore, the position of the X-ray source must be adjusted for each subject to be radiographed.

One example is the three-dimensional representation of the human vertebral column. The structural, positional and morphometric information that such representations offer is particularly interesting. It can for example help a surgeon in his pre-operative and post-operative diagnosis or it can be of the type favouring computer-aided surgical operations.

The only information of this type that a surgeon can easily gather comes from stereoradiographic systems that are available only in a very small number of hospitals. The equipment generally consist of a source and a radiographic film and a turntable upon which the patient is disposed in such away as to obtain several views at different angles of incidence. A calibration object is also added to the equipment.

It is in fact necessary to calibrate these views in such a way as to identify the geometrical parameters of the radiographic environment, that is to say to specify the relative positions of the X-ray source with respect to the film.

There are numerous methods of calibration but these generally depend on the description of the relative positions of the images and of the X-ray sources (or of the cameras). In order to determine the radiographic environment, these methods necessitate the management of 18 variables when carrying out calculations. In this case, the calibration object must surround the totality of the measurement volume which makes it particularly voluminous and bulky.

Furthermore, the patient must also be placed inside this measurement volume and can be made uncomfortable and put under stress due to the structure of the calibration object which surrounds him and/or to the length of the measuring and acquisition process.

It has also been proposed to place the patient lying down on a table, as if to scan him. However, unlike in the upright position, this measurement is not carried out under load and the curvatures of the vertical column (physiological or pathological) are thereby modified.

Furthermore, in order to obtain two views at different angles of incidence with only one image generating system, it is possible resort to a translation of the source (vertical or horizontal). But the two angles of incidence obtained are often close, which generates more errors in the 3D reconstruction. Moreover, the photographs thus obtained do not correspond to the radiographs currently used in clinical routine.

SUMMARY OF THE INVENTION

The inventors have therefore developed, which is the subject of the invention, a device interposed between the X-ray source and the vertical receiver of the said rays, making it possible to place the subject in two consecutive positions whilst holding the subject in a virtually immobile and stable position making it possible to cause the appearance in the radiographs obtained of a set of markers whose configuration is specific and whose relative positions in space are known and allowing an explicit calibration method for the calculation of the radiographic environment in such a way as to facilitate the calculations for the reconstruction of an image in three dimensions on the basis of two calibrated radiographs.

For this purpose, the stereoradiographic device intended to position a subject to be radiographed and to be interposed between an X-ray source and a vertical receiver of the said rays, comprising a horizontal table that is mobile in rotation and/or in unidirectional translation according to the invention is characterized in that the said table is orientable in two referenced positions at an angle of 90° with respect to each other and allowing the taking of two photographs corresponding to two positions of the subject that are orthogonal with respect to each other and in that the device also comprises a frame integral with the said horizontal table and possibly a complementary holding device for receiving the said subject and for holding him in a stable position, and at least three markers made of radio-opaque material disposed such that they are firmly attached to the said frame, one of the said markers being identified as the origin of an orthogonal three-dimensional reference system, the other markers being disposed in such a way as to provide, by projection on the axes of the said reference system, knowledge of at least one distance value, Lx, Ly and H respectively, between the said markers along the three axes X, Y and Z of the said reference system.

Moreover, due to the rotating table, two successive photographs, face and profile, are obtained which will also be able to be used as they are by the surgeon for a simple routine examination.

Furthermore, the disposition of a holding device constituted by the frame and/or by a complementary component, such as for example a pair of handles, makes it possible for the subject to find a stable upright position once mounted on said table, which makes it possible to keep the patient in a substantially identical position during the rotation of the rotating table in order to bring it from its first position to its second position after a rotation through 90° about a central axis of the table.

In this way calibrated radiographs are obtained since they are taken at two angles of incidence, with the subject as immobile as possible and containing markers allowing the calculation of the radiographic environment, that is to say the parameters describing the position and relative orientation of the film and of the source during the taking of the two photographs.

The photographs are therefore obtained according to two different virtual shooting axes.

The choice of angular rotation of the table is dictated both by practical constraints such that the radiographs can be used as they are by the practitioner and for the simplification of the calculations of the X images projected from a subject. Furthermore, many invariables are present: the distance between the receiver and the source remains constant, similarly the height of the source with respect to the device is also invariable by construction.

The set of markers, which constitutes the calibration means, is placed on the rotating table. This set therefore constitutes, by projection, vertical and horizontal lines which frame the radiographs of the subject.

The calibration parameters are then calculated plane-by-plane and view-by-view on the basis of a subset of markers (from those visible on the radiographs) unlike all the other methods which integrate the calculation of all of the constitutive points of the volume of the calibration object. The already calculated parameters or the invariables are then reused at each step.

Preferably, the markers will be situated in horizontal and vertical planes of the three-dimensional reference system whose first maker is the origin.

In a variant embodiment of the device according to the invention, the latter comprises three markers made of radio-opaque material, the first marker being identified as the origin of the said reference system, the second marker being disposed in a vertical plane including the said first marker and at a known height H with respect to the said first marker and at a distance Ly with respect to the vertical axis of the said reference system and the third marker being situated in a horizontal plane passing through the said first marker and perpendicular to the said first marker and at a distance Lx with respect to the said first marker.

In another variant embodiment, the device according to the invention comprises six markers made of radio-opaque material, the first marker being identified as the origin of the said reference system, four markers being disposed in a vertical plane containing the said first marker and forming two pairs of markers or dipoles, each of the dipoles being disposed vertically, the first dipole defining a straight line passing through the said first marker, the second dipole being situated at a distance Ly with respect to the said first dipole, the two markers of each dipole being separated by a height H and the sixth marker being situated in a horizontal plane passing through the said first marker and perpendicular to the said first marker and at a distance Lx with respect to the said first marker.

Finally, in a last variant embodiment of the device according to the invention, the latter comprises more than six markers made of radio-opaque material disposed in two parallel vertical lines and two horizontal lines perpendicular to the said vertical lines and one of the said markers is identified as the origin of the said reference system.

The use of a higher number of markers, but always disposed on lines along the axes of the reference system, renders the information Lx, Ly and H redundant.

Preferably, the said marker identified as the origin of the said three-dimensional reference system comprises a special marking in radio-opaque material making it possible to distinguish it simply from the other markers.

In particular, the said radio-opaque material is a steel.

The device according to the invention represents an integrated system which simultaneously allows the positioning of the patient, the projection of markers onto the films and the rotation of the assembly in order to obtain two photographs. This protocol is therefore perfectly compatible with the clinical protocol for taking radiographs (face, profile and fixed source)

This device can of course function with any type of X-ray source used in normal applications and in particular in the medical field and with any X-ray receiver, such as for example the conventional silver compound film holder, but also with digital X-ray detectors or any other device that is known or unknown at the present time.

This device proves simple to use for the operators, for example the radiographers, and does not necessitate adjustments other than those of the source and of the receiver as in conventional radiographic practice.

The structure of the device is open, easy to access particularly in the medial field for a patient who simply positions himself by holding himself using the frame and/or a complementary holding device optionally arranged for this purpose.

In a practical manner, it will be possible for the projections of the markers to be disposed on the edges of the radiograph such that the photograph is masked as little as possible due to their real physical positioning on the frame of the table.

The invention will be better understood on reading the following detailed description given with reference to the drawing for an application in the medical field:

BRIEF DESCRIPTION OF THE FIGS.

BRIEF DESCRIPTION OF THE INVENTION

Figure 1:
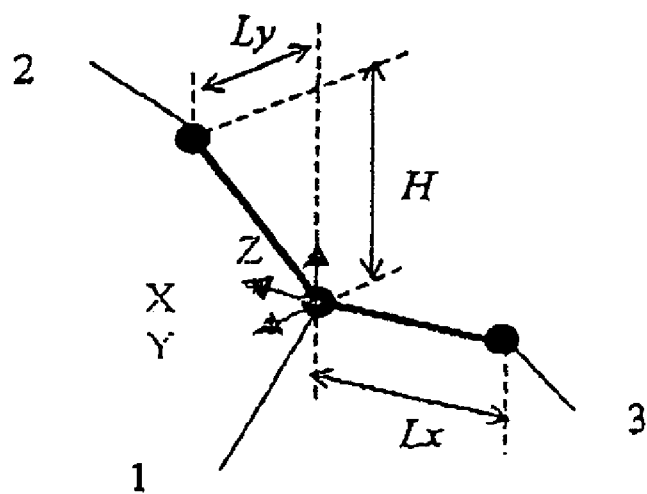
FIG. 1 shows a variant embodiment of the device according to the invention comprising only three markers.

In FIG. 1, a marker 1 is identified as the origin (0, 0, 0) of a three-dimensional reference system referring to the axes X, Y and Z. A second marker 2 is in the position defined by the coordinates (a, Ly, H) where the values of Ly and H must be known to the user and where the value of a can be any value. A third marker 3 is in the position defined by the coordinates (Lx, b, c) where the value Lx must be known by the user and where the values of b and c can be any values.

Figure 2:
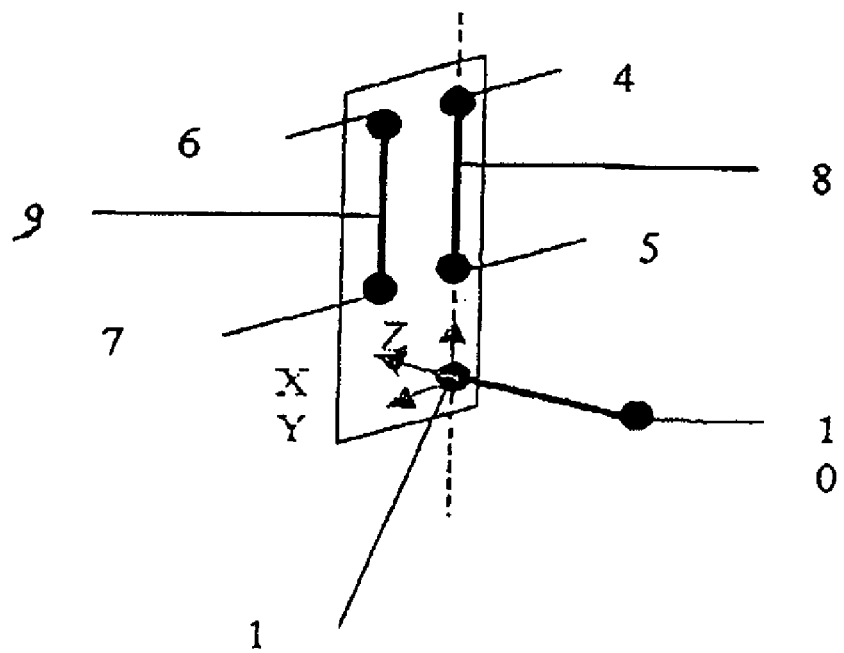
FIG. 2 shows another variant embodiment of the device according to the invention comprising six markers.

In FIG. 2, a marker 1 is identified as the origin of a three-dimensional reference system referring to the axes X, Y and Z. Four markers 4, 5, 6 and 7 are disposed in a vertical plane including the first marker 1 and forming two pairs 8 and 9 of markers, each of the pairs 8 and 9 is disposed vertically and the first pair 8 defines a straight line passing through the first marker 1. The second pair 9 is situated at a distance Ly with respect to the first pair 8. The two markers 4 and 5, and 6 and 7 respectively, of each pair 8 and 9 are separated by a height H and the fifth marker 10 is situated in a horizontal plane passing through the first marker 1 and perpendicular to the latter at a distance Lx with respect to the said first marker 1. These distances are fixed by construction and are known by the user.

Figure 3:
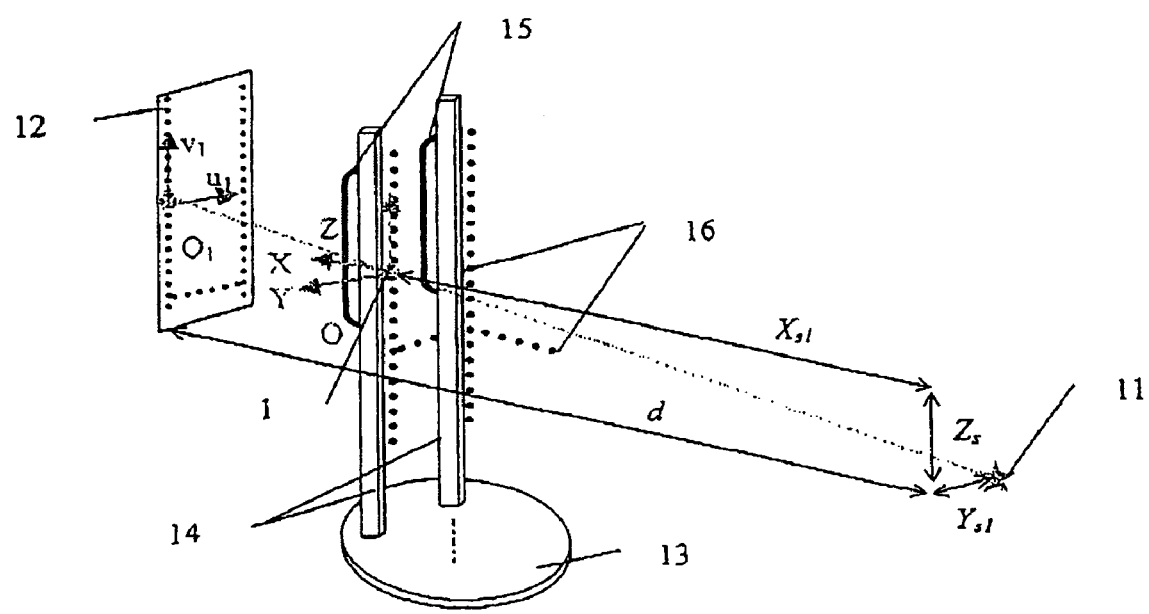
FIG. 3 shows another variant embodiment of the device according to the invention comprising a large number of markers.
Figure 4:
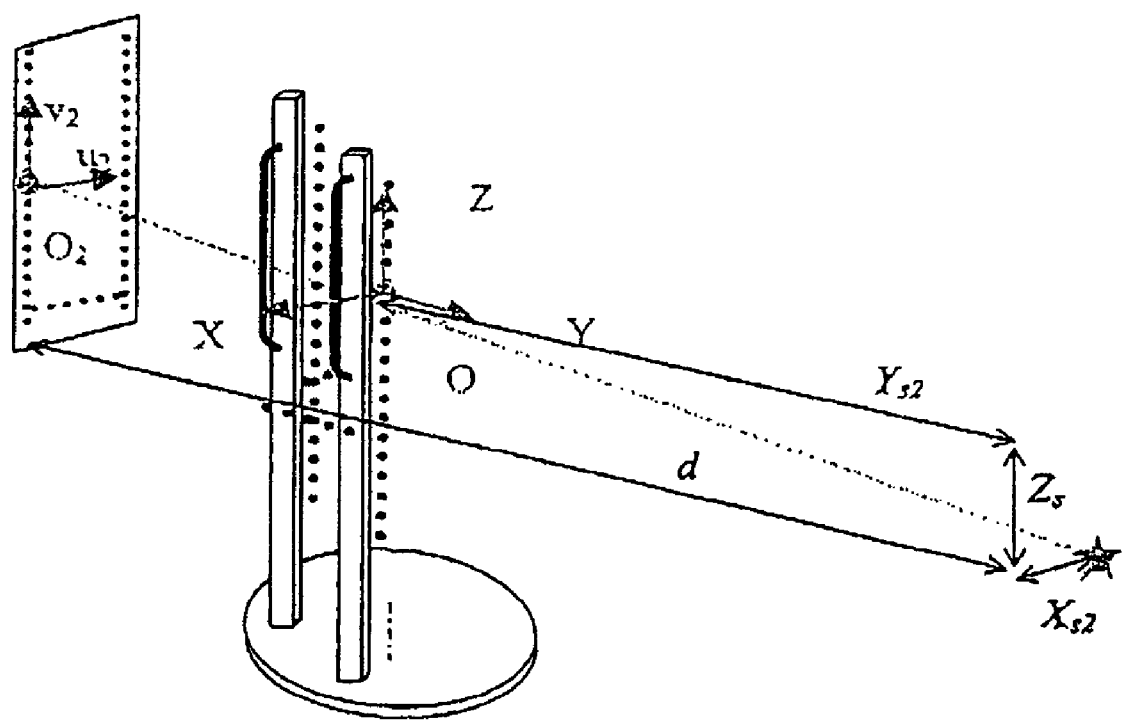
FIG. 4 shows the variant of FIG. 3 after rotation through 90°.

In FIGS. 3 and 4, the device according to the invention exhibits a set of more than six markers. Thus the device is placed between an X-ray source 11 and a vertical film holder 12 for collecting the X-rays emitted by the source 11. The device comprises a horizontal table 13 that is mobile in rotation due to conventional mechanical means and is orientable in two referenced positions at an angle of 90° with respect to each other and allowing the taking of two photographs that are orthogonal with respect to each other simply by rotating the table 3 about its axis. The 0 and 90 positions are marked for example by cooperation with locking stops, pins, colour markings or any other marking or locking device (not shown). A frame 14 integral with the horizontal table 13 is here equipped with a pair of handles 15 disposed as a possible complementary holding device designed to receive a subject whilst providing him with good balance and a position of rest that he will be able to retain during the rotation of the table 13 between the two shooting positions. Markers 16 made of radio-opaque material are disposed in a firmly connected manner on the frame 14 in at least two planes, horizontal and vertical, and thus the markers form a three-dimensional reference system in which the marker 1 is identified as the origin of the reference system, the other markers 16 being disposed in such a way as to provide knowledge of at least one value of distance, Lx, Ly and H respectively, between the said markers 16 along the three axes X, Y and Z.

FIG. 4 shows the device according to the invention after rotation through 90° and in position for taking a second photo.

The use of the device according to the invention is characterized in that the said device is placed between the said X-ray source 11 and the said X-ray receiver 12 in such a way that the vertical plane of the said three-dimensional reference system is parallel with the plane of the said receiver 12, in that the patient is placed on the said rotating table 13, in that the patient holds himself in a stable and fixed position of rest with the help of the said handles 15, in that a first photograph of the patient is taken in this position, in that that a rotation of the said rotating table 13 and possibly a translation of detachment or engagement of the device closest to the film is carried out, the said rotation being through 90° and integrally carrying the said frame 14, the said markers 1, 16 and the said patient and in that a second photograph of the said patient is taken.

The use of the device therefore proves to be particularly simple both for the practitioner and for the patient who is placed in a position of rest such that he remains immobile during the entire taking of the photographs even during the rotation or translation of the rotating table 13.

The X-ray source 11 is located facing the subject (who remains virtually immobile on the device) and then the system is put into two successive positions, indexed in such a way as to orient the axes of the spatial reference system (X, Y, Z) respectively parallel with and perpendicular to the plane of the radiographic film 12.

The radio-opaque markers 1, 16 are therefore projected in the radiographic image according to the following disposition: the marker 1 identified as the origin of the reference system and the vertical lines are visible in both of the images, one of the two horizontal lines is visible in one of the two images. It is the line that is parallel with the plane of the film.

The terms vertical and horizontal are applied to the lines obtained by connecting the markers 1, 4, 5, 6, 7, 10, 16 of the system for example in the case of a device according to the invention designed on the principle described and shown in FIGS. 2 and 3, or to the projections of the lines connecting the different markers 1, 2, 3 of the device on the axes of the three-dimensional reference system, such as for example in the case of a device designed on the principle described and shown in FIG. 1.

In this way, a reference system for each radiographic image can be defined, $R_{image1}$ ($O_1$, $u_1$, $v_1$, $w_1$) in FIG. 3 and $R_{image2}$ ($O_2$, $u_2$, $v_2$, $w_2$) in FIG. 4: that is to say the fixed origin on the projection of the marker identified as the origin of the reference system and the axes according to the projections of the vertical and horizontal lines.

Consequently, the stereoradiographic device makes it possible to determine specific conditions for the taking of radiographic images.

Firstly, the orientation of the spatial reference system ($R_{space}$) with respect to the two reference systems of the images ($R_{image1}$) and ($R_{image2}$) is fixed and known. The geometrical relationships between the three-dimensional two-dimensional coordinates (images 1 and 2) are established as a function of two known marks $m_1$ and $m_2$, imposed by the position of the rotating system. The matrix for changing from $R_{space}$ to $R_{image}$ is therefore defined by:

$$M = \begin{bmatrix} m_1 & m_2 & 0 \\ 0 & 0 & 1 \\ m_2 & -m_1 & 0 \end{bmatrix}$$

in which the pairs ($m_1$, $m_2$)=(1, 0) for the right lateral radiograph
($m_1$, $m_2$)=(−1, 0) for the left lateral radiograph
($m_1$, $m_2$)=(0, −1) for the posterior-anterior radiograph
($m_1$, $m_2$)=(0, 1) for the anterior-posterior radiograph.

Then, the distance between the radiographic film 12 (d) and the source 11 and the height of the latter with respect to the system ($Z_s$) remains unchanged during the successive taking of the two images, only the device is moved in rotation and possibly in translation.

Finally, for each photo, the position of the X-ray source 11 expressed with respect to the reference systems of the images ($u_{s1}$, $v_{s1}$, $u_{s2}$, $v_{s2}$ and d) and expressed with respect to the spatial reference system ($X_{s1}$, $Y_{s1}$, $X_{s2}$, $Y_{s2}$, and $Z_s$) are geometrically linked because of the construction of the projected reference systems.

Thus, these specific conditions, imposed by the device, make it possible to define the environment in which radiographic images are taken with a number of independent geometric unknowns limited to six (instead of eighteen in the general case).

It is therefore necessary to calibrate the radiographic shooting environment, that is to say to determine the relative positions of the images with respect to the X-ray sources, which can be described by six independent unknowns (for example).

The calculation of the independent parameters of the radiographic environment (as mentioned above or others) is carried out according to a specific calibration procedure making best use of the configuration of the radio-opaque markers (the projected information is different from one image to another and according to the axes in question) and by integrating the invariables and the geometrical relationships due to the construction of the abovementioned projected reference systems.

In particular, it is possible to calculate specifically $X_{s1}$, $Y_{s1}$, $X_{s2}$, $Y_{s2}$, $Z_s$ and d, as geometric parameters of the radiographic environment using a specific procedure, considering the vertical and horizontal planes of the two images separately and successively.

Depending on the configuration of the markers, the procedure can assume the following form:

The first step of the procedure consists in determining the parameters related to the vertical plane of image 1 (d, $Z_s$ and $Y_{s1}$) by considering the coordinates of the vertical lines of markers (expressed in $R_{space}$) and their projection (expressed in $R_{image1}$). The method of least squares is then used with the equations:

$$Y v_{s1} + v_1 Y_{s1} + \frac{Zd}{m_1 k} = v_1 Y \text{ and } v_{s1} = -\frac{Z_s d}{m_1 k Y_{s1}}$$

The second step of the procedure consists in determining the parameter related to the horizontal plane of image 1 ($X_{s1}$) by considering the coordinates of the horizontal lines of markers (expressed in $R_{space}$) and their projection (expressed in $R_{image1}$) as well as the parameters already calculated (d and $Y_{s1}$). Here again the method of least squares is used on:

$$Y u_{s1} + u_1 Y_{s1} + Xd = u_1 Y \text{ and } u_{s1} = -\frac{X_{s1} d}{Y_{s1}}$$

The third step of the procedure consists in determining the parameter related to the vertical plane of image 2 ($X_{s2}$) by considering the coordinates of the vertical lines of markers (expressed in $R_{space}$) and their projection (expressed in $R_{image2}$) and well as the already calculated parameters (d and $Z_s$)

The following is then used:

$$v_{s2} = \frac{Z_s d}{m_2 k X_{s2}} \text{ and } X v_{s2} + v_2 X_{s2} + \frac{Zd}{m_2 k} = v_2 X$$

and the following is obtained:

$$v_2 X_{s2}^2 + \left(\frac{Zd}{m_2 k} - v_2 X\right) X_{s2} - \frac{X Z_s d}{m_2 k} = 0$$

The fourth and final step of the procedure consists in determining the parameter related to the horizontal plane of image 2 ($Y_{s2}$) by considering the coordinates of the horizontal lines of markers (expressed in $R_{space}$) and their projection (expressed in $R_{image2}$) as well as the already calculated parameters (d and $X_{s2}$). The following is then used:

$$X u_{s2} + u_2 X_{s2} - Yd = u_2 X \text{ and } u_{s2} = \frac{Y_{s2} d}{X_{s2}}$$

The calculation of the geometric parameters of the environment is carried out by a computer program for which the entered input data is as follows:

the orientation of the radiographs taken on the device (posterior-anterior or anterior-posterior and right lateral or left lateral).

the coordinates of the markers of each image. These coordinates are obtained during a step of identification of the projection of the makers on the film, carried out by a standard method (table to be digitized or computer software after digitizing radiographic films).

the three-dimensional coordinates of the markers, obtained once and for all during the manufacture of the device (manufacturing data, verniers, sliding calliper gauges).

At the end of the program, all of the geometric parameters of the environment are calculated by an appropriate algorithm (the six independent parameters plus the others, derived or known a priori).

The present invention is not of course limited to the variant embodiments described above as non-limitative examples, nor to the variant implementations of the device according to the invention in the described methods.

It will thus be possible to combine the device according to the invention with, for example, a pressure table making it possible to determine the line of gravity of the body and to be able to use this information in correlation with that provided directly by the device according to the invention.

The invention claimed is:

1. A calibration system for a stereoradiographic device having an X-ray source and a vertical X-ray receiver, the calibration system comprising:
 a horizontal table which rotates between two reference positions that are separated by 90 degrees in a horizontal plane of the table;
 a vertical frame fastened to the horizontal table and symmetrical with an axis of rotation of the table, the frame accommodating a patient that remains stationary relative to the frame as the table is rotated between its two reference positions wherein corresponding X-ray photographs are taken;
 at least three markers made of radio opaque material firmly attached to the frame, one of the markers representing the origin of orthogonal X,Y and Z axes, a second of the markers located at a predetermined point along the X-Y axes, the third marker located at a known distance along the Z axis, the markers defining respective distances Lx, Ly or H relative to the origin.

2. The system of claim 1 wherein the second marker is located at a preselected distance H with respect to a first axis and a distance Ly with respect to a second axis; the third marker being located at a point along a third axis and in a plane that is parallel to the table.

3. The device according to claim 1, comprising six markers, the first marker representing the origin of the axes; four markers being disposed in a plane perpendicular to the table and containing the first marker, the four markers forming two parallel vertical dipoles; a first dipole defining a straight line passing through the first marker; the second dipole being situated at a distance Ly with respect to the first dipole; the two markers of each dipole being separated by a distance H from the origin; and a sixth marker being situated in a horizontal plane passing through the first marker at a distance Lx with respect to the first marker at the origin.

4. The device according to claim 1, comprising more than six markers disposed in two parallel vertical lines and two horizontal lines that are orthogonal to and intersect the vertical lines; and
   further wherein one of the six markers represents the origin of the axes.

5. The device according to claim 1 wherein the marker identifying the origin of the axes is made of a radio-opaque material that is distinguishable from all the other markers.

6. The device according to claim 1 wherein the radio-opaque material is made of steel.

7. A method for calibrating a stereoradiographic device for taking X-ray photographs of a patient positioned directly between an X-ray source and a vertical X-ray receiver, the method comprising the steps:
   providing a horizontal table which rotates between two reference positions that are separated by 90 degrees in a horizontal plane of the table;
   fastening a vertical frame to the horizontal table, the frame being symmetrical with an axis of rotation of the table, the frame accommodating a patient that remains stationary relative to the frame as the table is rotated between its two reference positions wherein corresponding X-ray photographs are taken;
   attaching at least three markers made of radio opaque material firmly to the frame, one of the markers representing the origin of orthogonal X,Y and Z axes, a second of the markers located at a predetermined point along the X-Y axes, the third marker located at a known distance along the Z axis, the markers defining respective distances Lx, Ly or H relative to the origin.

8. The method of claim 7 wherein the second marker is positioned at a preselected distance H with respect to a first axis and a distance Ly with respect to a second axis; the third marker being located at a point along a third axis and in a plane that is parallel to the table.

9. The method of claim 7, wherein six markers are provided, the first marker representing the origin of the axes; four markers being disposed in a plane perpendicular to the table and containing the first marker, the four markers forming two parallel vertical dipoles; a first dipole defining a straight line passing through the first marker; the second dipole being situated at a distance Ly with respect to the first dipole; the two markers of each dipole being separated by a distance H from the origin; and a sixth marker being situated in a horizontal plane passing through the first marker at a distance Lx with respect to the first marker at the origin.

10. The method according to claim 7, wherein than six markers are disposed in two parallel vertical lines and two horizontal lines that are orthogonal to and intersect the vertical lines; and
   further wherein one of the six markers represents the origin of the axes.

11. The method according to claim 7 wherein the marker identifying the origin of the axes is made of a radio-opaque material that is distinguishable from all the other markers.

* * * * *